(12) United States Patent
Fernwood et al.

(10) Patent No.: US 6,277,003 B1
(45) Date of Patent: Aug. 21, 2001

(54) GAS ABRASIVE PARTICLE APPARATUS AND VALVING THEREFOR

(75) Inventors: Mark S. Fernwood; Thomas S. Blake; Craig R. Bruns, all of Danville; Stephen L. Swihart, Walnut Creek, all of CA (US)

(73) Assignee: Danville Engineering, San Ramon, CA (US)

( * ) Notice: Subject to any disclaimer, the term of this patent is extended or adjusted under 35 U.S.C. 154(b) by 0 days.

(21) Appl. No.: 09/445,101
(22) PCT Filed: May 28, 1998
(86) PCT No.: PCT/US98/11040
§ 371 Date: Mar. 8, 2000
§ 102(e) Date: Mar. 8, 2000
(87) PCT Pub. No.: WO98/53954
PCT Pub. Date: Dec. 3, 1998
(51) Int. Cl.[7] .................................................. B24C 5/00
(52) U.S. Cl. ..................................... 451/91; 451/90; 433/88
(58) Field of Search ..................................... 451/28, 38, 40, 451/60, 75, 89, 90, 91, 99, 100, 102; 406/28, 29, 30, 75, 124, 141; 239/325, 346, 144, 311, 317; 222/161, 196; 433/88

(56) References Cited

U.S. PATENT DOCUMENTS 5,718,581    2/1998   Fernwood et al. .

FOREIGN PATENT DOCUMENTS

WO 93/19685    10/1993   (WO) .

*Primary Examiner*—Derris H. Banks
(74) *Attorney, Agent, or Firm*—Cooley Godward LLP

(57) ABSTRACT

An apparatus for dispensing a pressurized stream of gas having particles suspended therein, is described. A double acting pinch valve suitable for use in the apparatus is also described. The apparatus finds particular utility in the dental industry.

31 Claims, 9 Drawing Sheets

GAS ABRASIVE PARTICLE APPARATUS AND VALVING THEREFOR

TECHNICAL FIELD

This invention relates to gas abrasive technology. More particularly, it relates to methods and apparatus for supplying a gas stream of abrasive particles to abrade a surface and to control the flow of such a stream to the surface to be abraded. The invention is particularly useful for dental applications.

BACKGROUND

The use of gas abrasive in the dental industry has considerably reduced the pain and general unpleasantness involved in dental procedures. Traditional gas abrasive delivery systems worked much like a salt shaker. They were basically chambers which would be vibrated in order to force the abrasive out of the holes at the bottom of the chamber. Another type of gas abrasive delivery system vibrated the abrasive to flow up through a circular track to bring sand up through the top of the chamber. These systems had the common problem of excessive noise and vibration. Systems can be found which avoid the excessive noise and vibration by blowing gas over the top of the abrasive to create a dust cloud which could be blown or sucked out to the end piece. These systems had severe difficulty with abrasive flow control. The apparatus of this invention provides a gas abrasive delivery system having a more consistent flow pattern of the gas/abrasive stream. Also provided is a unique double-action pinch valve for controlling the flow of the gas/abrasive stream.

SUMMARY OF THE INVENTION

One aspect of this invention is an apparatus for dispensing a pressurized stream of gas having particles suspended therein, which apparatus comprises:
 a container having a top portion and a bottom portion for holding the particles in a powder form;
 a closure means for the container so that the container can be pressurized by a gas;
 an interior chamber inside the container having at least one abrasive particle passage towards the bottom of the interior chamber through which the abrasive particles can enter the interior portion of the interior chamber;
 a gas inlet line leading into the container;
 an interior tube located inside the container having inlet and outlet ends and connected at its inlet end to the gas inlet line, the outlet end of the interior tube being directed downwardly into the interior of the interior chamber; and
 an outlet passage leading from the interior of the interior chamber to the outside of the container.

Another aspect of this invention is a double acting pinch valve that comprises:
 an unitary container;
 gas inlet port leading into the container;
 a pinch bar having a first contact side and a second contact side;
 a first passage for a first flexible tube leading past the first contact side of the pinch bar;
 a second passage for a second flexible tube leading past the second contact side of the pinch bar;
 a tension means for retaining the pinch bar in a first position sufficient to pinch closed a first flexible tube in the first passage; and
 an air pressure actuatable means within the container that, upon providing a pressurized gas to the gas inlet port, moves the pinch bar from the first position to a second position sufficient to open the first flexible tube in the first passage and pinch closed the second flexible tube in the second passage.

Yet another aspect of this invention is a double acting pinch valve comprising:
 a unitary container;
 a gas inlet port leading into the container;
 a first, movable pinch bar having a first contact portion and a second contact portion;
 a first passage for a first flexible tube leading past the first contact portion of the movable pinch bar;
 a first pinch seat in contact with the second contact portion of the movable pinch bar;
 a second, fixed pinch bar;
 a second passage for a second flexible tube leading past the fixed pinch bar;
 a second pinch seat juxtaposed to the fixed pinch bar such that the second flexible tube is positioned therebetween;
 a translation means connected to the movable pinch bar;
 a first tension means associated with the translation means for retaining the translation means in a first position sufficient to maintain the movable pinch bar to hold open the first flexible tube in the first passage,
 a second tension means for maintaining the second pinch seat in a position sufficient to pinch closed the second flexible tube against the fixed pinch bar;
 an air pressure actuatable means within the container that, upon providing a pressurized gas to the gas inlet port, moves the translation means from the first position to a second position sufficient to compel the movable pinch bar to pinch closed the first flexible tube in the first passage and to simultaneously compel the first pinch seat to contact the second pinch seat and open the second flexible tube in the second passage.

Another aspect of this invention is an apparatus for directing a pressurized stream of gas/abrasive particles against a surface, which apparatus comprises:
 (a) a container having a top portion and a bottom portion for holding the particles in a powder form, the container having
  a closure means for the container so that the container can be pressurized by a gas;
  an interior chamber located inside the container having at least one abrasive particle passage towards the bottom of the interior chamber through which the abrasive particles can enter the interior portion of the interior chamber;
  a gas inlet line leading into the container;
  an interior tube located inside the container having inlet and outlet ends and connected at its inlet end to the gas inlet line, the outlet end of the interior tube being directed downwardly into the interior of the interior chamber; and
  an outlet passage leading from the interior of the interior chamber to the outside of the container.
 (b) a handpiece with a nozzle for directing a pressurized stream of gas/particles against a surface,
 (c) a transmission tube connecting the handpiece and the outlet passage from the container, wherein the transmission tube has a valve between the outlet passage and the handpiece nozzle to regulate the flow of gas/particles stream therethrough, and (d) a source of pressurized gas connected to the gas inlet line leading into the container.

Another aspect of this invention is a gas abrasive apparatus for directing a pressurized stream of gas/abrasive particles against a surface, which apparatus comprises:

(a) a source of a pressurized stream of abrasive particles suspended in a gas;

(b) a handpiece with a nozzle for directing the pressurized stream of gas-suspended particles against a surface;

(c) a first flexible transmission tube connecting the handpiece with the pressurized stream of gas-suspended particles;

(d) a double acting pinch valve that acts upon the first flexible transmission tube and that comprises:
  a unitary container;
  a gas inlet port leading into the container;
  a first, movable pinch bar having a first contact portion and a second contact portion;
  a first passage for the first flexible transmission tube leading past the first contact portion of the first pinch bar;
  a first pinch seat in contact with the second contact portion of the first pinch bar;
  a second, fixed pinch bar;
  a second passage for a second flexible transmission tube leading past the second pinch bar;
  a second pinch seat juxtaposed to the second pinch bar such that the second flexible tube is positioned therebetween;
  a translation means connected to the first pinch bar;
  a first tension means associated with the translation means for retaining the translation means in a first position sufficient to maintain the first pinch bar to hold open the first flexible tube in the first passage,
  a second tension means for maintaining the second pinch seat in a position sufficient to pinch closed the second flexible tube against the second pinch bar;
  an air pressure actuatable means within the container that, upon providing a pressurized gas to the gas inlet port, moves the translation means from the first position to a second position sufficient to compel the first pinch bar to pinch closed the first flexible tube in the first passage and to simultaneously compel the first pinch seat to contact the second pinch seat and open the second flexible tube in the second passage; and (e) a second flexible transmission tube having its inlet end connected in fluid communication at a junction downstream of the pinch valve and leading through the second passage of the pinch valve to the outlet end of the second, flexible transmission tube.

Another aspect of this invention is an apparatus for producing a gaseous stream having abrasive particles suspended therein, which apparatus comprises:

(a) a source of a pressurized stream of abrasive particles suspended in a gas;

(b) a handpiece with a nozzle for directing the pressurized stream of gas-suspended particles against a surface; and (c) a first flexible transmission tube connecting the handpiece with the pressurized stream of gas-suspended particles;

wherein the improvement comprises: a double acting pinch valve to close the first flexible transmission tube and simultaneously allow exhaust of the stream through a second flexible transmission tube.

Yet another aspect of the invention pertains to an apparatus for dispensing a pressurized stream of gas having particles suspended therein onto a surface, which apparatus comprises:

a source of particles;

a source of pressurized gas;

a particle-mixing means supplied with the particles and pressurized gas, for combining the particles and the pressurized gas to produce a gas/particle stream;

a first flexible transmission tube leading from the particle-mixing means to a delivery means for delivering the gas/particle stream to the surface;

a double-acting pinch valve positioned between the particle-mixing means and the delivery means, and fitted with the first tube and a second flexible transmission tube, which is joined to the first tube at a junction between the valve and the delivery means; and a valve-activating means;

wherein when the valve is activated and in a first position, the second tube is closed and the gas/particle stream flows through the first tube to the surface; and when the valve is not activated and in a second position, the first tube is closed and the gas/particle stream flows through the second tube and is vented.

Other aspects of the invention will be apparent to one of skill in the art upon reading the following specification and claims.

DETAILED DESCRIPTION AND PRESENTLY PREFERRED EMBODIMENTS

One aspect of this invention is an apparatus for dispensing a pressurized stream of gas having particles suspended therein, which apparatus comprises
  a container having a top portion and a bottom portion for holding the particles in a powder form;
  a closure means for the container so that the container can be pressurized by a gas;
  an interior chamber located inside the container having at least one abrasive particle passage towards the bottom of the interior chamber through which the abrasive particles can enter the interior portion of the interior chamber;
  a gas inlet line leading into the container;

an interior tube located inside the container having inlet and outlet ends and connected at its inlet end to the gas inlet line, the outlet end of the interior tube being directed downwardly into the interior of the interior chamber; and an outlet passage leading from the interior of the interior chamber to the outside of the container.

As used herein, the terms "gas/abrasive particles", "gas/abrasive", "gas/particle" and "gas-suspended particles" are used interchangeably to mean a mixture of gas and abrasive particles, typically a pressurized stream of gas having abrasive particles suspended therein.

Figure 1A:
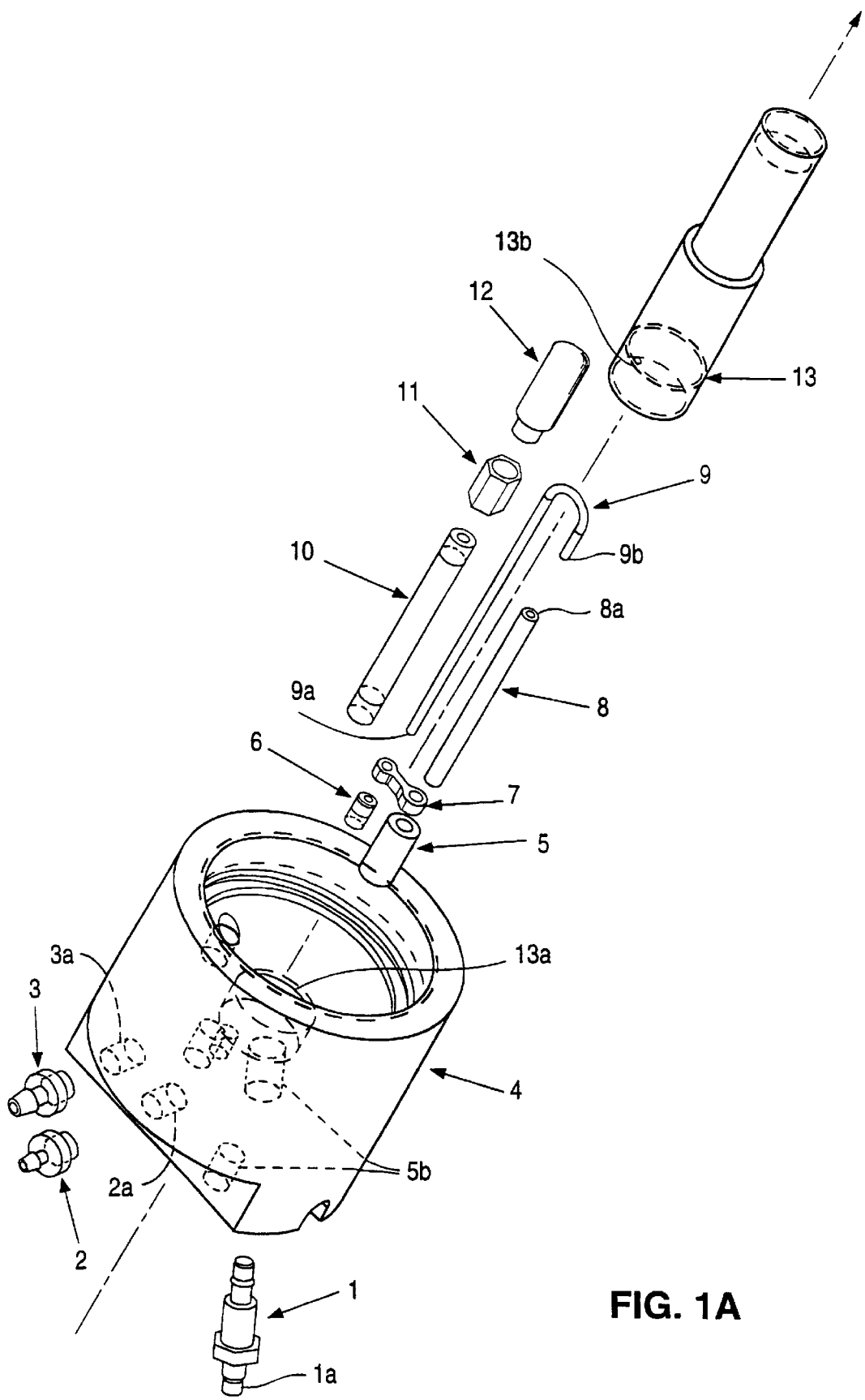
FIGS. 1A and 1B offer an exploded view of an apparatus of this invention for dispensing a pressurized stream of gas having particles suspended therein.
Figure 1B:
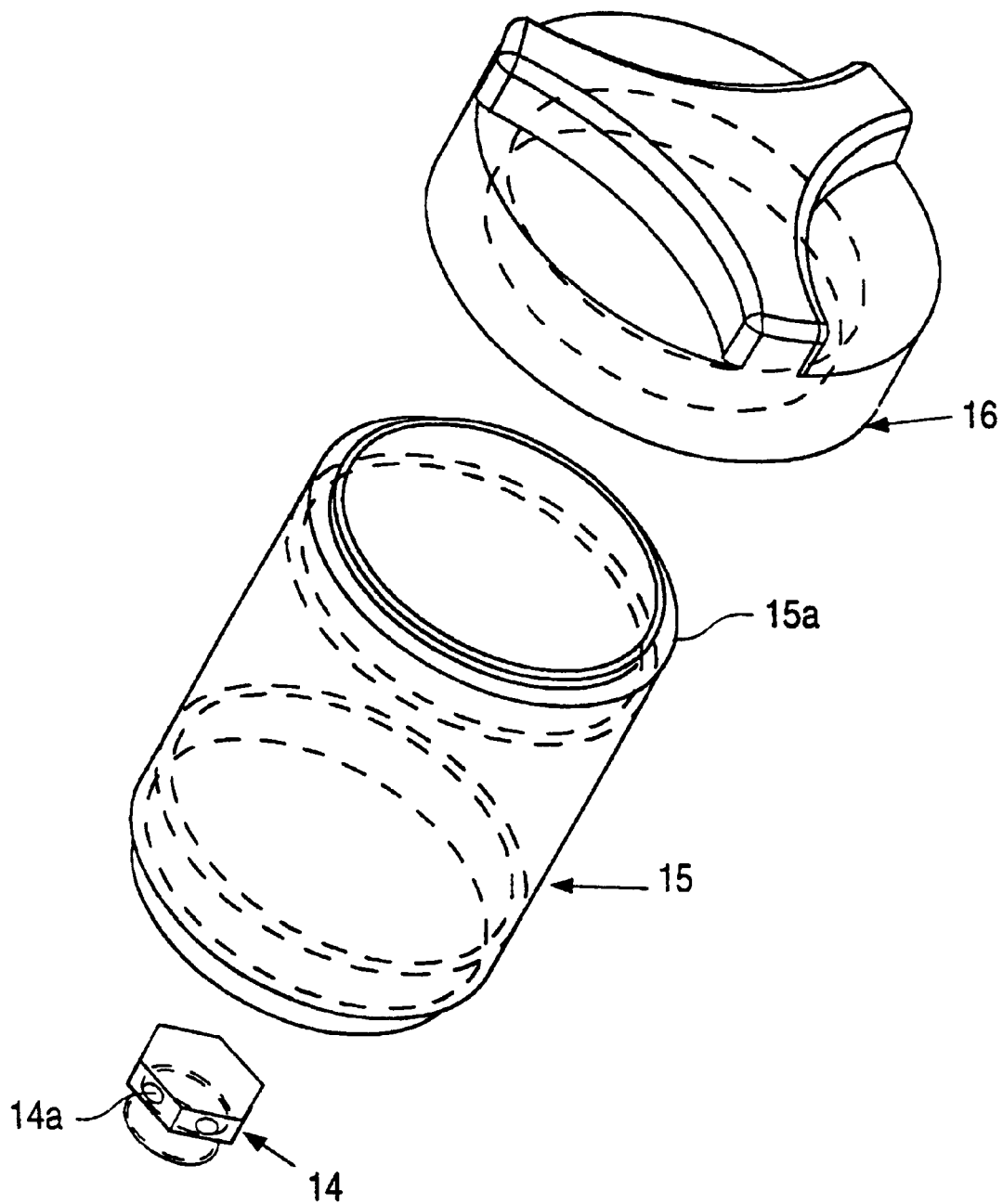

A more detailed description of certain preferred aspects of the apparatus of this invention is shown in FIGS. 1A and 1B. In general, the apparatus comprises a container having a top portion and a bottom portion. The container in this particular representation is shown in three parts. The bottom portion is shown as 4, while the middle portion which is connected thereto, is shown as 15 and upper portion 15a is shown as part of 15 as well. The container has a closure means shown as 16 so that the container may be pressurized by a gas. The closure means 16 may be threaded to screw onto the upper portion 15a. may snap fit, may have a clamp to hold closure 16, or other equivalent structure to achieve closure so that the container may be pressurized by a gas. Inside the container is located an interior chamber shown as 13 which in this representation is shown to fit into the bottom portion of the container. Thus, the interior chamber 13 is shown as fitting into receptacle 13a in the bottom portion 4 of the container. While the interior chamber is shown to fit into the bottom of the container, the interior chamber can be positioned anywhere within the interior of the container. Thus for example, it could be positioned towards the side of the container, attached in the middle of the container or attached to the closure means 16. It is preferred to have it attached to the bottom of the container to maximize the number of particles that can flow into the interior portion of the interior chamber. Once the interior chamber is positioned as shown in FIG. 1, it can be seen that it has at least one abrasive particle passage 13b toward the bottom of the interior chamber through which abrasive particles can enter the interior portion of the interior chamber. Although FIG. 1A only illustrates one abrasive particle passage 13b, interior chamber 13 preferably has at least four such passages for optimal particle flow. Such passages have a diameter large enough to permit particle flow and typically have a diameter at least twice the diameter of the particles. Thus, when the container is fully assembled the abrasive particles will be positioned within the container and the majority of the particles will be located between the outside wall of interior chamber 13 and the inside wall of the middle portion 15. Thus, by gravity flow or by a type of Venturi effect, the particles will flow through the passage 13b and into the interior of interior chamber 13. Preferably, the interior chamber 13 will be closed at its top by a cap 14. The cap will have passageways 14a that will allow gas to flow into the interior chamber or out of the interior chamber depending upon the relative pressure inside middle portion 15. In general, it is preferred that the passages 14a are of a smaller dimension when larger abrasive particles are used in the container and the passage is large when smaller particle sizes are used in the container. Passages 14a are shown in FIG. 1B as having a fixed diameter. It is understood however, that cap 14 may be designed such that these passages have an adjustable diameter that can be varied to suit the particular requirements of the user. In such an event, it is preferable that the apparatus be designed so that the passage 14a diameters may be adjusted remotely.

A gas inlet line 2 leads into the container through an internal passageway shown as 2a An interior tube 9 is positioned to be connected to line 2 through connector 6 and optional holder 7. The gas inlet line here is shown as being located at the bottom portion of the container and internal to the interior chamber 13. However, the gas inlet line may be located anywhere through any wall of the container so long as its function is performed appropriately. Thus, the tube 9 has an inlet end 9a and an outlet end 9b. The outlet end of interior tube 9 is directed downwardly into the interior of chamber 13. In FIG. 1, tube 9 is shown to fit into the bottom of bottom portion 4. However, tube 9 can be positioned anywhere within the interior of the container. Thus for example, it could be positioned towards the side of the container or attached in the middle of the container. The only limitation is that it must be positioned such that the outlet end 9b is directed downwardly into the interior of chamber 13.

In addition, an outlet passage leading from the interior of chamber 13 to the outside of the container is shown as upright outlet tube 8 connected to fitting 5 which fits into the bottom of container 4 connecting to passageway 5b and outlet 1 shown in the FIG. 1A as being disconnected is from the container. The inlet end 8a of tube 8 is positioned lower than the outlet end 9b of tube 9. Tube 8 can be aligned with tube 9, as shown in FIG. 1A or it can be in an offset position. Inlet end 8a can be positioned above or below the level of abrasive particles contained within interior chamber 13. When end 8a is positioned above the particle level, less abrasive particles will be suspended in the gas stream than when end 8a is positioned below the particle level.

In addition, a passage defined by connector 3 through passageway 3a provides an inlet and outlet for the flow of gas to pressure up the container and to pressure down the container. Thus, the gas may enter through inlet 3 and passage 3a to tube 10 and fitting 11 topped by a filter device 12, which prevents any abrasive particle backflow.

In operation, the container is assembled and the closure means 16 connected so that the container can be pressurized by a gas. Pressurized gas flows in through inlet 2 and passage 2a to tube 9 and out the outlet of tube 9 at 9b. The particles which are held within the container as previously mentioned flow through passageway 13b. As the gas flows downwardly into the bottom of the interior chamber the particles entering through passageway 13b are suspended and are forced out outlet tube 8 through the outlet 5b and 1 to a transmission line where it is directed to a handpiece with a nozzle that can be directed against a surface to abrade the surface.

Numerous particle types and size are contemplated as part of the invention. For dental applications of the invention typical particles will be in the range of 2–100 microns, more typically 25–50 microns in diameter; suitable particle materials include alumina, aluminum oxide and calcium carbonate.

Figure 7:
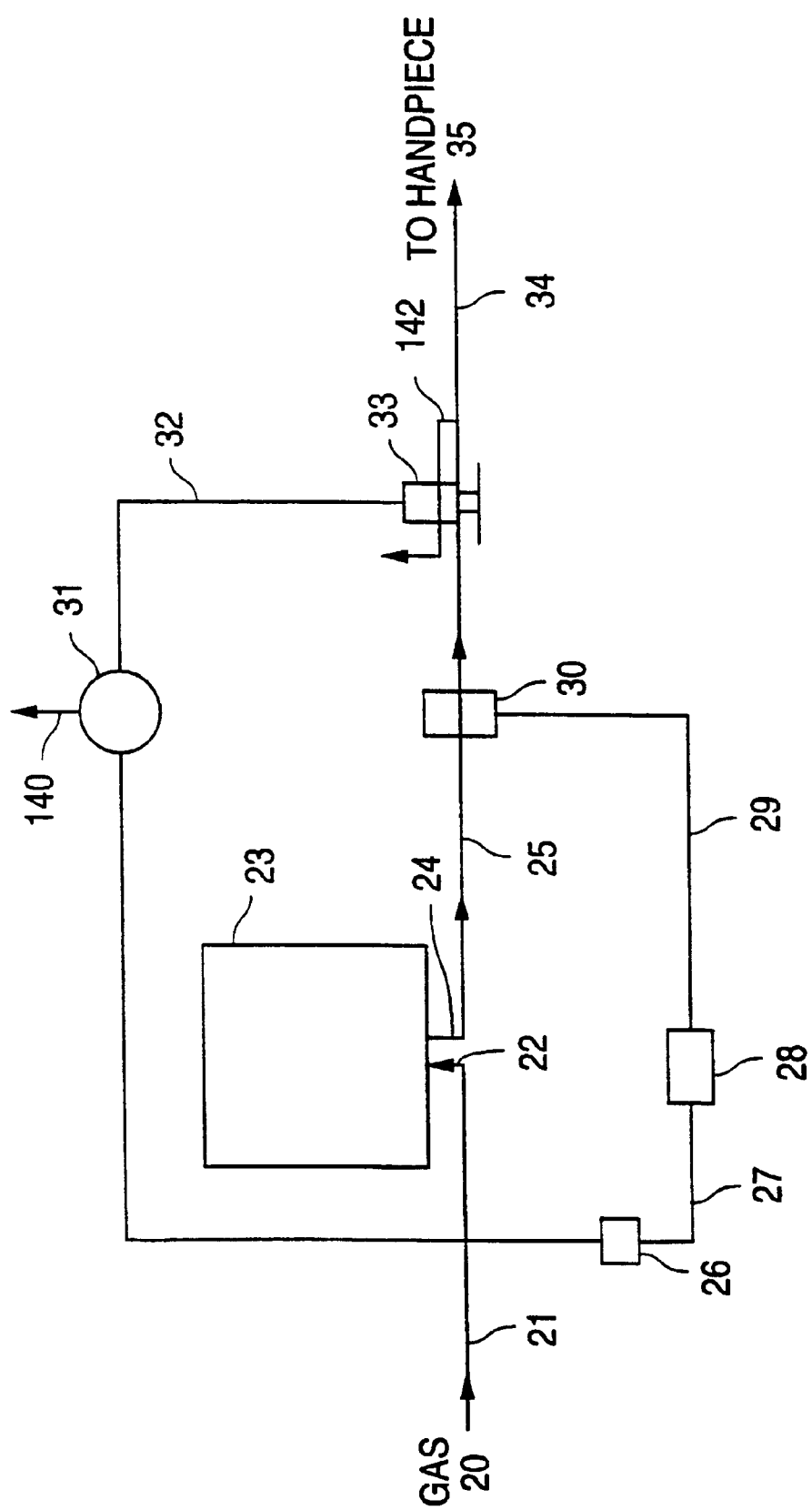
FIG. 7 is a schematic design for gas abrasive system in accordance with this invention.

A schematic shown in FIG. 7 shows a system employing the apparatus in its simplest form. A source of pressurized gas (which may be carbon dioxide, nitrogen, argon, air or other suitable gas) is provided. The apparatus of the invention can operate under a broad range of gas pressures, depending upon the particular application. For example, 35–160 p.s.i. are suitable ranges for dental applications. The gas 20 goes through a transmission line 21 to the inlet 22 to the container shown in FIG. 1 or a similar container 23. The particles are suspended as discussed hereinbefore and exit container 23 through outlet 24 into transmission line 25. Optionally and preferably, there is a mixing chamber 30 through which additional gas can be transmitted through line 27 through filter 28 and ultimately line 29. The amount of gas added will adjust the number of particles in the line going to the handpiece and can adjust the rate at which the abrasion will take place. The amount of added gas may be varied by including an adjustable valve 26 in line 29. The gas-particle suspension leaves mixing chamber 30 to go to valve 33. Preferably this is a pinch valve that operates on a flexible line 34 leading to handpiece 35. The pinch valve may be operated by an off/on switch or three-way valve 31 which allows gas to flow through line 32 and turn it on or to not have gas flowing through the line and turned off. Alternatively, it can be turned on with no gas flow and off with gas flow. The system is also provided with vents 140 and 142. Once the gas/abrasive particle stream goes to the handpiece and exits a nozzle to the surface to be abraded. This design is particularly valuable for the use in dentistry in removing resins, adhesives, plaque. and wearing away the enamel of the teeth to get to the dentin level. For this application, air is preferably the gas used.

Figures 2, 3:
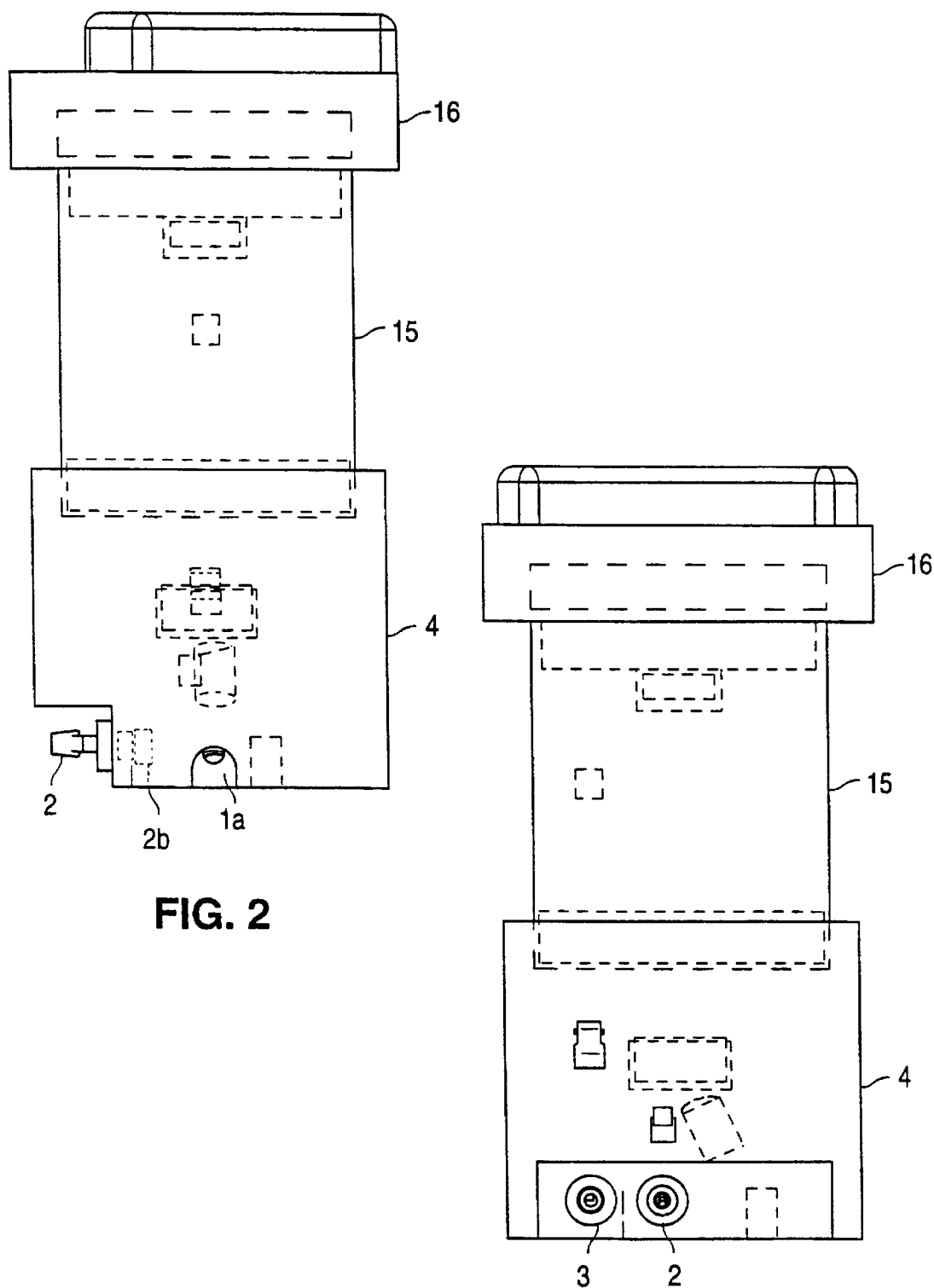
FIG. 2 is a side view of the assembled apparatus of FIG. 1.
FIG. 3 is a front view of the assembled apparatus of FIG. 1.

Turning now to FIG. 2, one can see a side view of the container shown in FIG. 1. Here, the middle portion 15 is shown as fitting into bottom portion 4 and closure means 16. The gas inlet line or nipple is shown as 2 with the internal passage showing in lighter lines as 2b. The outer tip 1a of outlet nipple 1 shown in FIG. 1A is shown in FIG. 2.

FIG. 3 is an end-on view of the container filly assembled. Again, the bottom portion 4 integrates with middle portion 15 and closure means 16. The gas inlet 2 is shown next to the optional and additional gas inlet/outlet connector 3.

Figure 4:
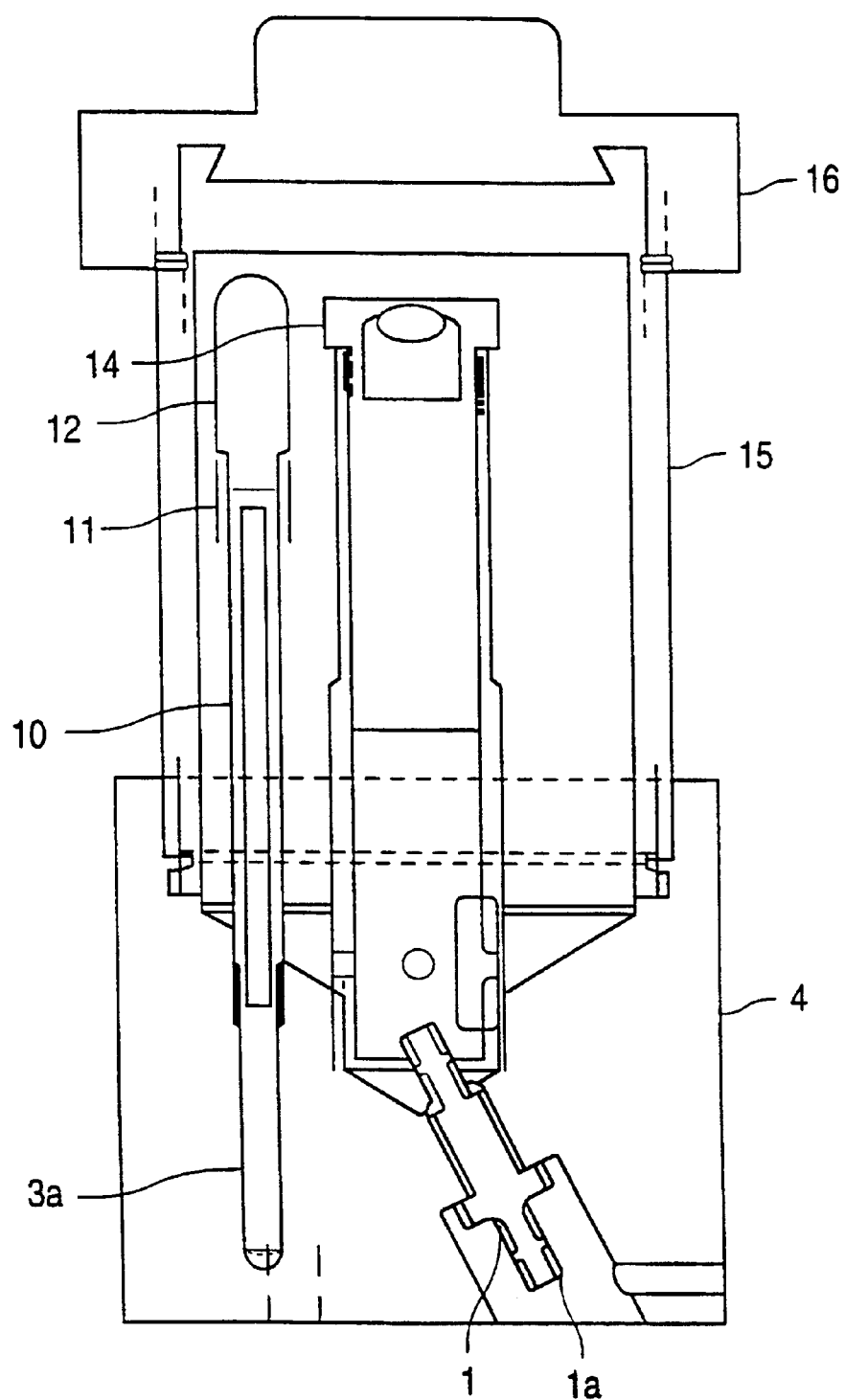
FIG. 4 is a cross-section view of the assembled apparatus of FIG. 1.

Turning now to FIG. 4, one sees a cross-sectional view of the apparatus shown in FIG. 1 but fiully assembled. The numerals shown here are consistent with those used in FIG. 1 for the various parts of the invention. Note that the cross-section of interior chamber 13 does not illustrate the components contained therein.

Figure 5:
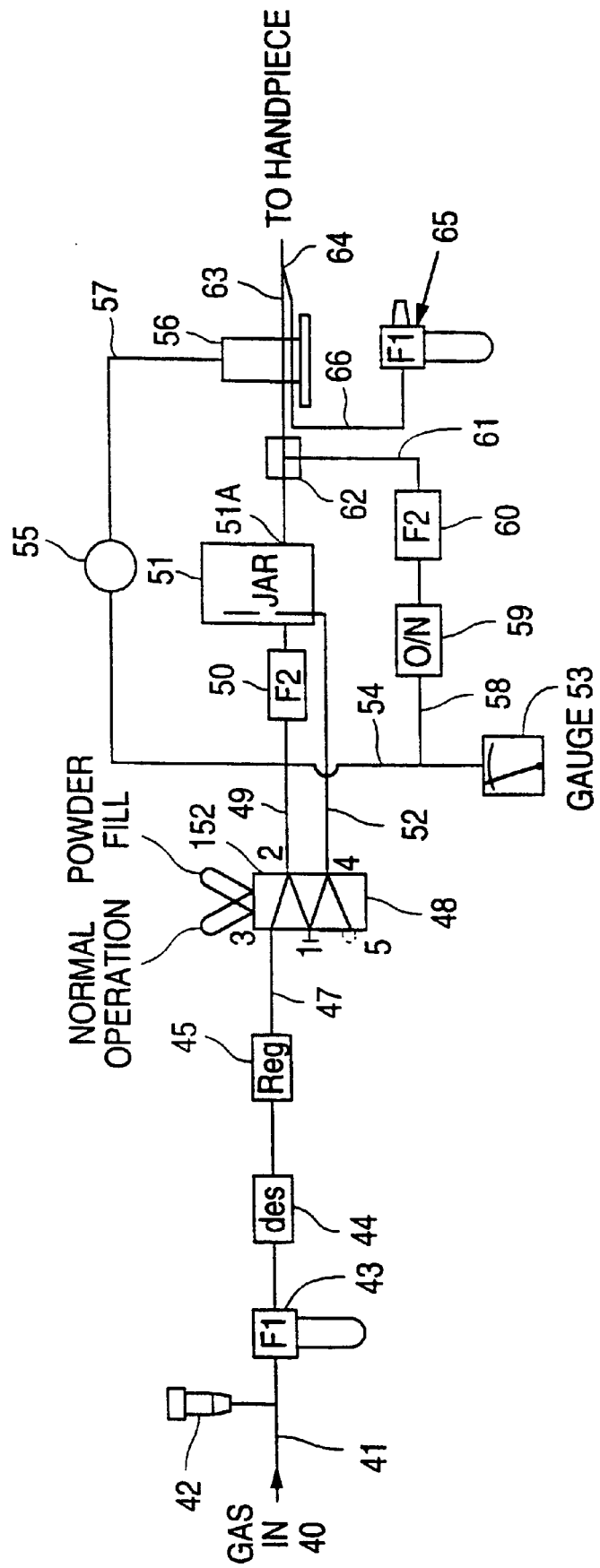
FIG. 5 is a schematic design for a dental gas abrasive system in accordance with this invention.

Turning now to FIG. 5, one sees a preferred aspect in a schematic diagram of the apparatus shown in FIG. 1 with a preferred valve which also forms part of this invention. Here. gas source 40 is shown as entering line 41 that has a pressure relief valve 42 located therein. A particulate filter, preferably with a manual drain is shown as 43 to filter out any large particles that might be in the gas line. The gas goes through the filter 43 and into the desiccant filter 44 to remove water from the gas line. The gas, preferably air, goes then into a manual regulator 45 and thence into line 47 where it goes through a valve 48 that allows the system to operate normally in one position (shown as normal operation or the "pressurized mode") and in the "powder fill" position, which allows the container shown as 51 to be filled by removing the closure means at the top of the container. When valve 48 is closed, it also allows the system to vent by depressurizing container 51. The gas/particle stream flows through an additional filter 50, which captures the particles, to transmission line 49. Clean gas is then released through vent 152. Container 51 is pressurized by air or gas passing through the multi-positioned valve 48 and transmission line 52 to container 51, where the stream of gas having the suspended particles is formed and goes out the outlet line 51a to the mixing chamber 62. At this point, additional gas can be added to the gas-particle stream to dilute the level of particulate matter in the stream. Gauge 53 registers the pressure in line 54 and 58. The gas goes through line 58 to needle valve 59 and through an additional filter 60 to line 61 as is needed. Filter 60 prevents backflow into valve 59. Generally needle valve 59 will be a manually adjusted needle valve that will be adjusted on a time-to-time basis as needed. Valve 59 can also be pulse logic (referred to as "pulse-duty cycle control mechanism" in PCT Patent Application PCT/US96/06676 filed May 9, 1996, which is incorporated herein by reference), solenoid valve, or other electronic flow control means. Once the diluted stream leaves the mixing chamber 62 it goes through line 63 through a unique pinch valve 56 which is discussed hereinafter. This pinch valve is regulated in a dental setting by foot switch 55 which provides gas to flow through line 57 to actuate the valve and allow the gas-particle stream to flow to the handpiece or be cut off and bleed to the abrasive collection container 65. It can be seen that a junction 64 is located downstream of the valve 56. At that junction a line 66 flows to the abrasive collection container.

The invention contemplates several modifications to the embodiment illustrated in FIG. 5. The function of manual regulator 45 can also be achieved using an electronic control, pulse logic, a proportional valve, a pressure control means or a pressure regulator. all of which are contemplated by the instant invention. As indicated above, line 49 leads to an additional filter 50. However, this invention also contemplates line 49 leading to a 4-way manifold for distribution of the gas throughout the system. Such a manifold could be positioned on line 49 between valve 48 and filter 50 or, alternately, between filter 50 and container 51.

The foot switch 55/valve 56 system is shown in FIG. 5 as being at the end closest to the handpiece. This system can also be positioned between filter 43 and filter 44, or between filter 44 and manual regulator 45. Either of these positions is preferred when higher line pressure to valve 56 is desired to insure proper closure, particularly when valve 56 is a double acting pinch valve such as is shown in FIG. 6 as valve 70.

It will be apparent to one of ordinary skill in art that the apparatus of this invention for dispensing a pressurized stream of gas having particles suspended therein may be used in numerous system configurations known in the art. For example, configurations shown in U.S. patent application Ser. No. 08/438,355 filed May 9, 1995 and PCT Patent Application PCT/US96/06676 filed May 9, 1996, are particularly useful and are incorporated herein by reference. Other configurations that may be used are shown in U.S. Pat. Nos. 5,350,299; 5,330,354; 4,708,534; and PCT/US93/02939, all of which are also incorporated herein by reference. In each of these, a key aspect of the configuration is combining the apparatus with a conduit means in fluid communication with the outlet passage and connectable to a handpiece and nozzle for directing the stream of the gas-particle suspension against a surface to abrade a portion of the surface. Preferably the combination will include a handpiece having a nozzle for directing the gas-particle stream against a surface, wherein the handpiece is connected to the outlet passage of the chamber by a transmission tube through which the gas-particle mixture flows, the transmission tube having a flow control means, such as a valve, therein to regulate the flow of the gas-particle stream therethrough. Preferably the transmission tube has (i) a junction upstream of the flow control means for mixing additional gas with the gas-particle stream to reduce the concentration of the gas-particle stream prior to reaching the flow control means. Particularly valuable is a combination wherein the transmission tube has a junction downstream of the flow control means for a conduit having a second flow control means associated therewith to allow the gas-particle stream to drain from the transmission line when the first flow control means is closed and the second flow control means is open.

Figure 6:
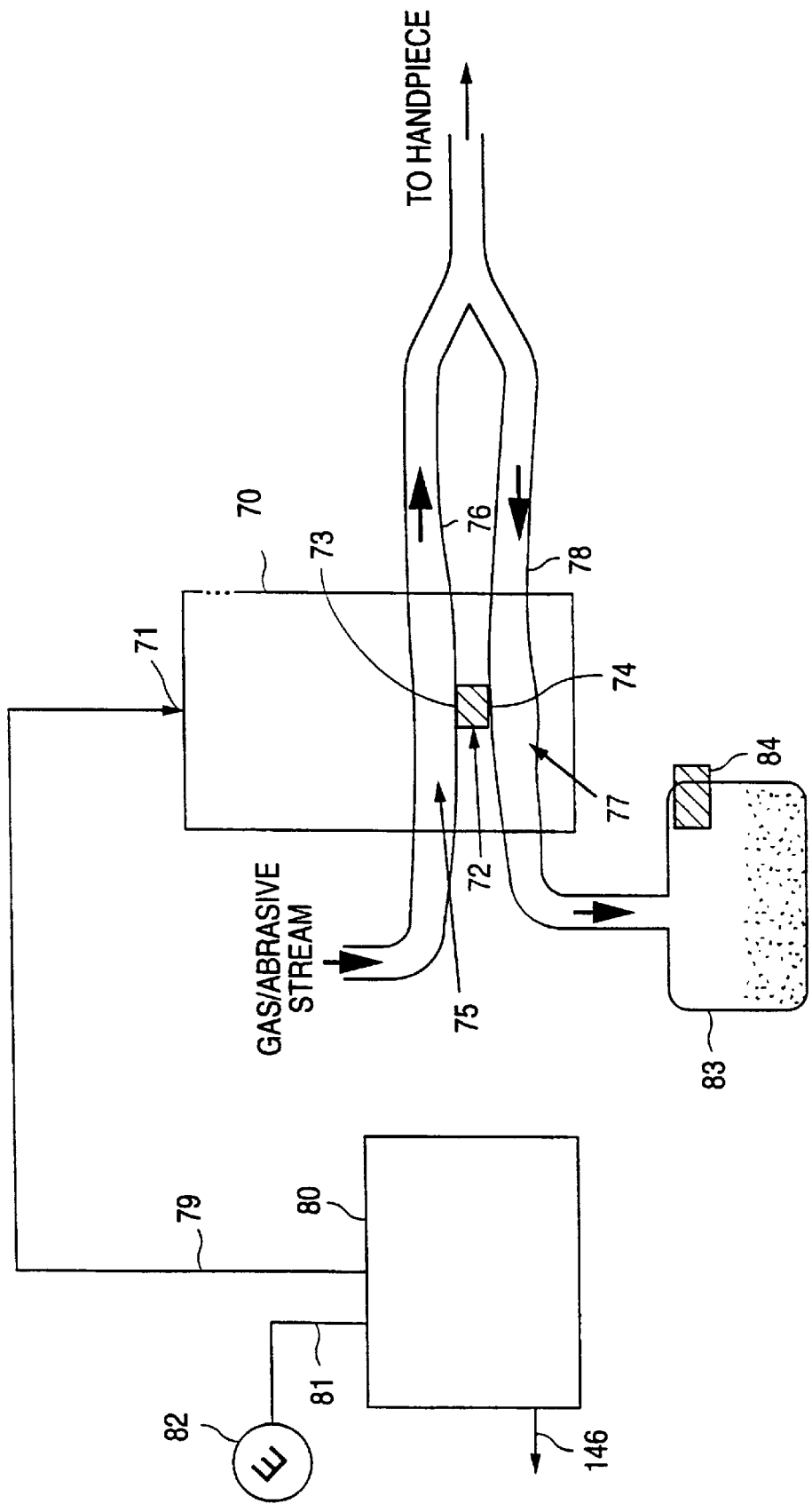
FIG. 6 is a schematic design for the unique double-action pinch valve in accordance with this invention.

Turning now to FIG. 6, one sees a preferred double-acting pinch valve that is usefuil in the apparatus. In general, the double acting pinch valve of this invention is a single unit. This unit includes an unitary container, a gas inlet port leading into the container, and a pinch bar having a first contact side and a second contact side. Leading past the first contact side of the pinch bar is a first passage for a first flexible tube and leading past the second contact side of the pinch bar is a second passage for a second flexible tube. A tension means such as a spring (not shown) retains the pinch bar in a first position sufficient to pinch closed a first flexible tube in the first passage. Upon providing a pressurized gas to the gas inlet port, a gas pressure actuatable means within the container moves the pinch bar from the first position to a second position sufficient to open the first flexible tube in the first passage and pinch closed the second flexible tube in the second passage. Preferably, the pinch valve is combined with a pressurized gas source that is intermittently controllable and is connected to the gas inlet source.

In FIG. 6 the double-acting pinch valve is shown as 70. In general, it is a unitary container or valve that has a gas inlet port 71 leading into the container. A pinch bar 72 is associated with the container having a first contact side 73 and a second contact side 74 to the bar. While the pinch bar 72 is shown as substantially rectangular, it should be recognized that it could be circular, oval or polygonal in cross-section. The pinch valve has a first passage 75 for a first flexible tube 76 leading past the first contact side of the pinch bar. A second passage 77 for a second flexible tube 78 leading past the second contact side 74 is associated with the pinch bar. A tension means, not shown, retains the pinch bar in a first position sufficient to pinch closed the first flexible tube 76. This tension means can be a spring designed to push or pull the bar into position. In addition, the valve has a gas pressure actuatable means within the container that, upon providing a pressurized gas to the gas inlet port 71, moves the pinch bar 72 from the first position closing tube 76 to a second position which opens tube 76 but closes tube 78. Thus, in operation a gas/abrasive mixture would enter the line 76 in accordance with the arrow shown. If the pinch bar has closed tube 76 going through passage 75, then no gas/abrasive stream will flow to the handpiece. However, if the pinch bar is put into the open position, then passage 75 opens and passage 77 and flexible tube 78 close, so the only flow will be to the handpiece. Once the gas/abrasive stream is flowing to the handpiece and the stream is shut off by activating the pinch valve to close tube 76, tube 78 is then opened and the residual pressurized gaslabrasive stream flows through tube 78 and into spent abrasive collection chamber 83. The collection chamber 83 is fitted with a filter element 84 that allows the gas to go out but retains the abrasive inside the container. The double-action pinch valve can be actuated by the use of a foot pedal which have a source of gas 82 which flows through line 81 to a foot pedal valve 80. When the foot pedal is pressed to allow gas through the valve 80 and into line 79, it flows through inlet 71 to the double-acting pinch valve to force the pinch valve into a position opening tube 76 and allowing the air or gas/abrasive stream to flow to the handpiece. Valve 80 is also fitted with vent 146.

It will be recognized that the double-acting pinch valve of this invention has broad applicability for ensuring flow through only one of two adjacent, parallel, flexible tubes while flow through the other is shut off. While the pinch valve of this invention finds particular use with the gas abrasive apparatus described in detail herein, it can be used with any other gas abrasive dispensing apparatus known in the art. Referring again to FIG. 5, an apparatus for dispensing a pressurized stream of gas having particles suspended therein onto a surface, would comprise a source of particles (51); a source of pressurized gas (52); a particle-mixing means (also 51), for combining the particles and pressurized gas to produce a gas/particle stream; a first flexible transmission tube (63) leading from the particle-mixing means (51) to a delivery means for delivering the gas/particle stream to the surface (shown here as a handpiece); and a double-acting pinch valve (56) positioned between (51) and the delivery means, and fitted with the first tube (63) and a second flexible transmission tube (66), which is joined to the first tube (63) at a junction (64) between valve (56) and the delivery means. The valve also has an activating means, shown here as a foot switch (55). When valve (56) is activated and in a first position, the second tube is closed and the gas/particle stream flows through the first tube to the surface; and when valve (56) is not activated and in a second position, the first tube is closed and the gas/particle stream flows through the second tube and is vented, preferably to a waste container.

Examples of such gas abrasive apparati include those shown in U.S. Pat. No. 3,852,918 issued Dec. 10, 1974; U.S. Pat. No. 4,487,582 issued Dec. 11, 1984; U.S. Pat. No. 2,814,877 issued Dec. 3, 1957; U.S. Pat. No. 3,139,705 issued Jul. 7, 1964; U.S. Pat. No. 3,149,759 issued Sep. 22, 1964; U.S. Pat. No. 3,344,524 issued Oct. 3 1967; U.S. Pat. No. 3,631,631 issued Jan. 4, 1972; U.S. Pat. No. 4,067,150 issued Jan. 10, 1978; U.S. Pat. No. 4,708,534 issued Nov. 24, 1987; and the like. All of these are incorporated herein by reference.

Figure 8:
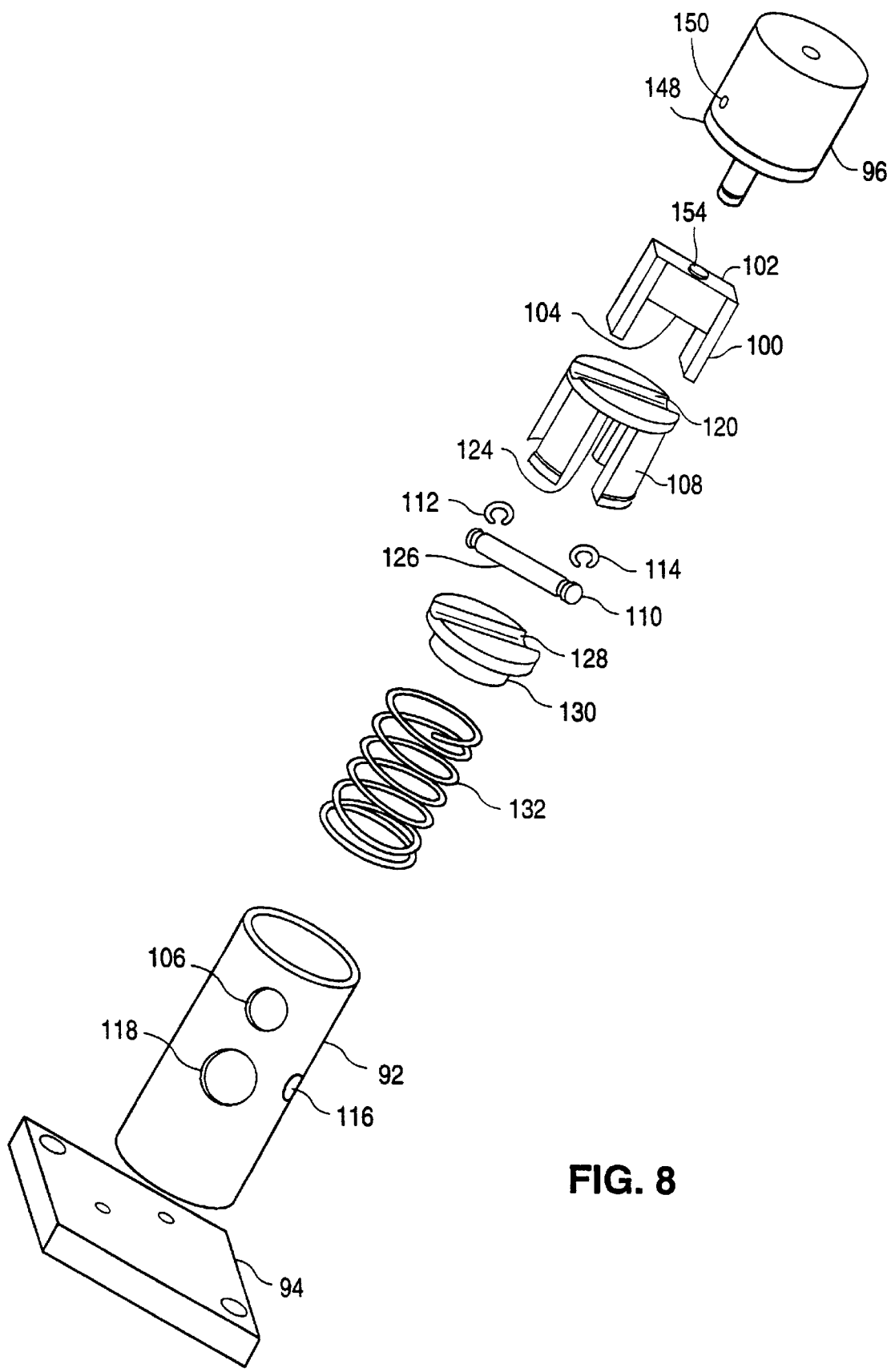
FIG. 8 is an exploded view of a double acting pinch valve of this invention.
Figure 9:
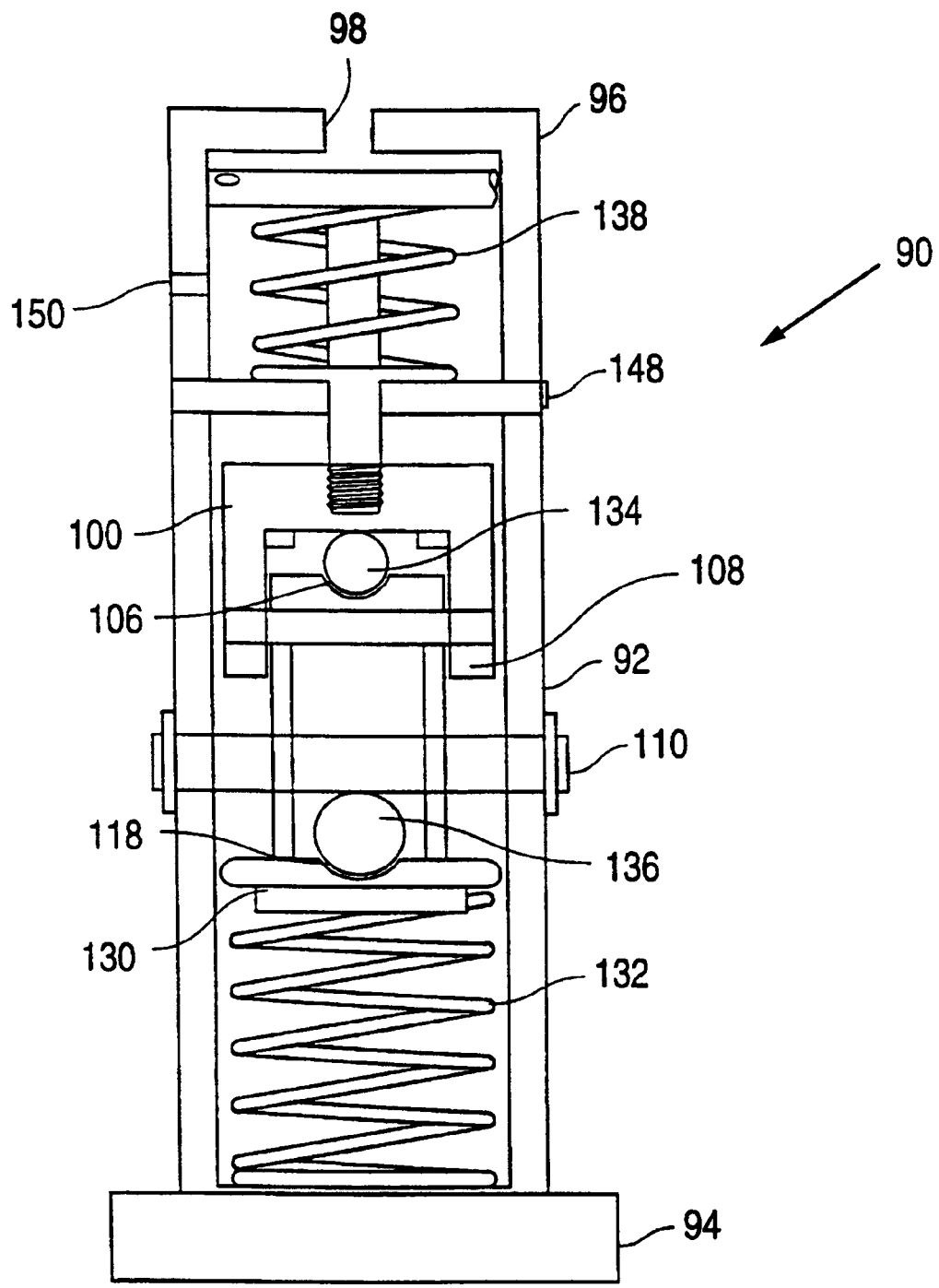
FIG. 9 is a side view of the assembled valve of FIG. 8.

FIGS. 8 and 9 shown another preferred double-acting pinch valve that is useful in the apparatus. Turning to FIG. 8, the double acting pinch valve is a single unitary container 90. This unit includes a body tube 92, a body plate 94 and a translation means 96, which moves downwards towards the plate during operation. Translation means 96 operates to move the pinch valve components along the length of the body tube 92, and can be, for example, a piston, pneumatic cylinder or an electronic solenoid. Translation means 96 is connected to a top pinch bar 100, for example, by a threaded hole 154, and is provided with a vent 150 and removable plate 148. Plate 148 facilitates assembly of container 90.

Movable pinch bar 100 is associated with the container and has a first contact portion 102 and a second contact portion 104. The pinch bar can be of any desired shape such as rectangular, circular, oval or polygonal in cross-section. The pinch valve has a first passage 106 for a first flexible tube, not shown, which leads past the second contact portion 104 of pinch bar 100 and the first contact portion 120 of a top pinch seat 108. Pinch seat 108 is also in contact with the second contact portion 104.

A fixed lower pinch bar 110 is also associated with the container, fitting into hole 116 in body tube 92 and held in place by hold means 112 and 114. This pinch bar can also be of any desired shape such as rectangular, circular, oval or polygonal in cross-secti6n. The first contact portion 122 of pinch bar 110 is in contact with the second contact portion 124 of seat 108. The pinch valve also has a second passage 118 for a second flexible tube, not shown, which leads past the second contact portion 126 of pinch bar 110 and the first contact portion 128 of a lower pinch seat 130. Pinch seat 130 is also in contact with the second contact portion 126.

Turning to FIG. 9, the single unitary container 90 is shown in assembled cross-section. In operation, the first flexible tube 134 in first passageway 106 would lead to a spent abrasive collection chamber and the second flexible tube 136 in second passageway 118 would function to carry the airlabrasive particles to the handpiece. A first tension means 138 is associated with translation means 96 and retains the translation means in a first position sufficient to maintain pinch bar 100 to hold open the first flexible tube 134. A second tension means 132 retains pinch seat 130 in a first position sufficient to hold closed the second flexible tube 136 by pinching it against pinch bar 110. Tension means 132 and 138 are shown as springs, but may be other equivalent devices.

In addition, the valve 90 has a gas pressure actuatable means that, upon providing a pressurized gas to the gas inlet port 98, moves translation means 96 from its first position to a second position sufficient to compel pinch bar 100 to pinch closed the first flexible tube 134 and to simultaneously move pinch seat 130 to a second position, causing pinch seat 130 to no longer be in contact with pinch bar 110, and open the second flexible tube 136. Thus, in operation pressurized gas would enter port 98, moving translation means 96 to its second position, closing passage 106/flexible tube 134 and opening passage 118/flexible tube 136 such that the gas/abrasive stream will flow to the handpiece. However, if the pinch bar is put into the first position, then passage 106/tube 134 opens and passage 118/tube 136 close, and flow to the handpiece ceases. Once the gas/abrasive stream is flowing to the handpiece and the stream is shut off by activating the pinch valve to close tube 136, tube 134 is then opened and the residual pressurized gas/abrasive stream flows through tube 134 and into a spent abrasive collection chamber. As is shown in FIG. 6, the collection chamber would be fitted with a flit that allows the gas to go out but retains the abrasive inside the container.

Once in operation, translation means 96 moves the top pinch bar 100 and pinch seat 108 down the body tube 92 in unison, pinching flexible tube 134 closed. In this position, translation means 96 also maintain pinch seat 108 in contact with pinch seat 130, such that pinch seat 130 is not in contact with pinch bar 110 and flexible tube 118 remains open. When the pressurized gas flow to the translation means ceases, pinch seat 108 ceases to exert pressure on pinch seat 130, allowing seat 130 to come into contact with pinch bar 110 and pinching flexible tube 118 closed. Simultaneously, pinch seat 108 ceases to be in contact with pinch bar 100 and flexible tube 134 opens.

Having completed the description of the apparatus in both its broad aspects, as well as its preferred aspects. one of ordinary skill in the art may identify other aspects of the invention that would be apparent and obvious to one upon reading the specification. Such aspects of the invention are meant to be included within the scope of this disclosure and claims.

The subject matter claimed is:

1. Apparatus for dispensing a pressurized stream of gas having particles suspended therein, which apparatus comprises:

a container having a top portion and a bottom portion for holding the particles in a powder form;

a closure means for the container so that the container can be pressurized by a gas;

an interior chamber inside the container having at least one abrasive particle passage towards the bottom of the interior chamber through which the abrasive particles can enter the interior portion of the interior chamber;

a gas inlet line leading into the interior container;

an interior tube located inside the container having inlet and outlet ends and connected at its inlet end to the gas inlet line, the outlet end of the interior tube being directed downwardly into the interior of the interior chamber; and an outlet passage leading from the interior of the interior chamber to the outside of the container.

2. The apparatus of claim 1 wherein the interior tube is located within the interior chamber.

3. The apparatus of claim 2 wherein the interior tube is connected at its inlet end to the gas inlet line and is designed to have its outlet end at the upper portion of the interior chamber directed toward the bottom of the interior chamber.

4. The apparatus of claim 2 wherein the interior chamber has a cap at the upper portion to close the interior chamber.

5. The apparatus of claim 4, wherein the upper portion of the interior chamber has small passages for gas to pass through.

6. The apparatus of claim 1 wherein the inlet line is located at the bottom portion of the container.

7. The apparatus of claim 1 wherein, when the container is filled with abrasive particles located primarily in the space defined by the interior wall of the container and the exterior wall of the interior chamber and gas at greater than atmospheric pressure is forced into the inlet line, abrasive particles flow through the abrasive particle passage into the interior of the interior chamber and are suspended in the gas entering the interior chamber from the outlet end of the interior tube to form a gas-particle suspension, which is then forced out the outlet passage of the interior chamber.

8. The apparatus of claim 7 in combination with a conduit means in fluid communication with the outlet passage and connectable to a handpiece and nozzle for directing the stream of the gas-particle suspension against a surface to abrade a portion of the surface.

9. The apparatus of claim 7 in combination with a handpiece having a nozzle for directing the gas/particle stream against a surface, wherein the handpiece is connected to the outlet passage of the interior chamber by a transmission tube through which the gas/particles mixture flows, the transmission tube having a flow control means therein to regulate the flow of the gas/particles stream therethrough.

10. The apparatus of claim 9 wherein the transmission tube has a junction upstream of the flow control means for mixing additional gas with the gas/particles stream to reduce the concentration of the gas/particles stream prior to reaching the flow control means.

11. The apparatus of claim 9 wherein the transmission tube has a junction downstream of the flow control means for a conduit having a second flow control means associated therewith to allow the gas/particles stream to drain from the transmission line when the first flow control means is closed and the second flow control means is open.

12. A gas abrasive apparatus for directing a pressurized stream of gas/abrasive particles against a surface, which apparatus comprises:

(a) a container having a top portion and a bottom portion for holding the particles in a powder form, the container having:

a closure means for the container so that the container can be pressurized by a gas;

an interior chamber located inside the container having at least one abrasive particle passage towards the bottom of the interior chamber through which the abrasive particles can enter the interior portion of the interior chamber;

a gas inlet line leading into the container;

an interior tube located inside the container having inlet and outlet ends and connected at its inlet end to the gas inlet line, the outlet end of the interior tube being directed downwardly into the interior of the interior chamber; and an outlet passage leading from the interior of the interior chamber to the outside of the container;

(b) a handpiece with a nozzle for directing a pressurized stream of gas/particles against a surface;

(c) a transmission tube connecting the handpiece and the outlet passage from the container, wherein the transmission tube has a valve between the outlet passage and the handpiece nozzle to regulate the flow of gas/particles stream therethrough; and (d) a source of pressurized gas connected to the gas inlet line leading into the container.

13. The apparatus of claim 12 wherein the interior tube is located within the interior chamber.

14. The apparatus of claim 13 wherein the interior tube is connected at its lower end to the gas inlet line and is designed to have its outlet end at the upper portion of the interior chamber directed toward the bottom of the interior chamber.

15. The apparatus of claim 13 wherein the interior chamber has a cap at the upper portion to close the interior chamber.

16. The apparatus of claim 15, wherein the upper portion of the interior chamber has small passages for gas to pass therethrough.

17. The apparatus of claim 12 wherein the inlet line is located at the bottom portion of the container.

18. The apparatus of claim 12 wherein, when the container is filled with abrasive particles located primarily in the space defined by the interior wall of the container and the exterior wall of the interior chamber and gas at greater than atmospheric pressure is forced into the inlet line, abrasive particles flow through the abrasive particle passage into the interior of the interior chamber and are suspended in the gas entering the interior chamber from the outlet end of the interior tube to form a gas/particle suspension, which is then forced out the outlet passage of the interior chamber and into the transmission tube.

19. The apparatus of claim 12 wherein the transmission tube has ajunction upstream of the flow control means for mixing additional gas with the gas/particles stream to reduce the concentration of the gas/particles stream prior to reaching the control valve.

20. The apparatus of claim 12 wherein the transmission tube has a junction downstream of the flow control means for a conduit having a second flow control means to allow the gas/ particles stream to drain from the transmission line when the first flow control means is closed and the second flow control means is open.

21. A double acting pinch valve that comprises:
an unitary container;
a gas inlet port leading into the container;
a pinch bar having a first contact side and a second contact side;
a first passage for a first flexible tube leading past the first contact side of the pinch bar;
a second passage for a second flexible tube leading past the second contact side of the pinch bar,
a tension means for retaining the pinch bar in a first position sufficient to pinch closed a first flexible tube in the first passage,
an air pressure actuatable means within the container that, upon providing a pressurized gas to the gas inlet port, moves the pinch bar from the first position to a second position sufficient to open the first flexible tube in the first passage and pinch closed the second flexible tube in the second passage.

22. The pinch valve of claim 21 in combination with a pressurized gas source that is intermittently controllable and is connected to the gas inlet source.

23. The combination of claim 22 that further comprises:
a first flexible tube that is (i) positioned in the first passage, (ii) in fluid communication with a source of a pressurized stream of gas having particles suspended therein, the source being upstream of the pinch valve, and (iii) connectable to a handpiece having a nozzle for the pressurized stream of suspended particles; and a second flexible tube having its inlet end connected in fluid communication at a junction downstream of the pinch valve and leading through the second passage of the pinch valve to the outlet end of the second flexible tube.

24. The combination of claim 23 that further comprises a particle collection chamber attached to the outlet end of the second tube wherein the pinch valve is positioned between the collection chamber and the junction.

25. A double acting pinch valve comprising:
a unitary container;
a gas inlet port leading into the container;
a movable pinch bar having a first contact portion and a second contact portion;
a first passage for a first flexible tube leading past the first contact portion of the movable pinch bar;
a first pinch seat in contact with the second contact portion of the movable pinch bar;
a fixed pinch bar;
a second passage for a second flexible tube leading past the fixed pinch bar;
a second pinch seat juxtaposed to the fixed pinch bar such that the second flexible tube is positioned therebetween;
a translation means connected to the movable pinch bar;
a first tension means associated with the translation means for retaining the translation means in a first position sufficient to maintain the movable pinch bar to hold open the first flexible tube in the first passage,
a second tension means for maintaining the second pinch seat in a position sufficient to pinch closed the second flexible tube against the fixed pinch bar;
an air pressure actuatable means within the container that, upon providing a pressurized gas to the gas inlet port, moves the translation means from the first position to a second position sufficient to compel the movable pinch bar to pinch closed the first flexible tube in the first passage and to simultaneously compel the first pinch seat to contact the second pinch seat and open the second flexible tube in the second passage.

26. A gas abrasive apparatus for directing a pressurized stream of gas/abrasive particles against a surface, which apparatus comprises:

(a) a source of a pressurized stream of abrasive particles suspended in a gas;

(b) a handpiece with a nozzle for directing the pressurized stream of gas-suspended particles against a surface;

(c) a first flexible transmission tube connecting the handpiece with the pressurized stream of gas-suspended particles;

(d) a double acting pinch valve that acts upon the first flexible transmission tube and that comprises:
a unitary container;
a gas inlet port leading into the container;
a first, movable pinch bar having a first contact portion and a second contact portion;
a first passage for the first flexible transmission tube leading past the first contact portion of the first pinch bar;
a first pinch seat in contact with the second contact portion of the first pinch bar;
a second, fixed pinch bar;
a second passage for a second flexible transmission tube leading past the second pinch bar;
a second pinch seat juxtaposed to the second pinch bar such that the second flexible tube is positioned therebetween;
a translation means connected to the first pinch bar;
a first tension means associated with the translation means for retaining the translation means in a first position sufficient to maintain the first pinch bar to hold open the first flexible tube in the first passage,
a second tension means for maintaining the second pinch seat in a position sufficient to pinch closed the second flexible tube against the second pinch bar;
an air pressure actuatable means within the container that, upon providing a pressurized gas to the gas inlet port, moves the translation means from the first position to a second position sufficient to compel the first pinch bar to pinch closed the first flexible tube in the first passage and to simultaneously compel the first pinch seat to contact the second pinch seat and open the second flexible tube in the second passage; and
(e) a second flexible transmission tube having its inlet end connected in fluid communication at a junction downstream of the pinch valve and leading through the second passage of the pinch valve to the outlet end of the second, flexible transmission tube.

27. The apparatus of claim 26 that further comprises a particle collection chamber attached to the outlet end of the second flexible transmission tube with the pinch valve positioned between the collection chamber and the junction.

28. The apparatus of claim 26 wherein the source of the pressurized stream of abrasive particles suspended in a gas is an apparatus comprising:
a container having a top portion and a bottom portion for holding the particles in a powder form;
a closure means for the container so that the container can be pressurized by a gas;
an interior chamber located inside the container having at least one abrasive particle passage towards the bottom of the interior chamber through which the abrasive particles can enter the interior portion of the interior chamber;
a gas inlet line leading into the container;
an interior tube located inside the container having inlet and outlet ends and connected at its inlet end to the gas inlet line, the outlet end of the interior tube being directed downwardly into the interior of the interior chamber; and
an outlet passage leading from the interior of the interior chamber to the outside of the container.

29. An apparatus for producing a gaseous stream having abrasive particles suspended therein, which apparatus comprises:
(a) a source of a pressurized stream of abrasive particles suspended in a gas;
(b) a handpiece with a nozzle for directing the pressurized stream of gas-suspended particles against a surface; and
(c) a first flexible transmission tube connecting the handpiece with the pressurized stream of gas-suspended particles;
wherein the improvement comprises: a double acting pinch valve to close the first flexible transmission tube and simultaneously allow exhaust of the stream through a second flexible transmission tube.

30. Apparatus for dispensing a pressurized stream of gas having particles suspended therein onto a surface, which apparatus comprises:
a source of particles;
a source of pressurized gas;
a particle-mixing means supplied with the particles and pressurized gas, for combining the particles and the pressurized gas to produce a gas/particle stream;
a first flexible transmission tube leading from the particle-mixing means to a delivery means for delivering the gas/particle stream to the surface;
a double-acting pinch valve positioned between the particle-mixing means and the delivery means, and fitted with the first tube and a second flexible transmission tube, which is joined to the first tube at a junction between the valve and the delivery means; and
a valve-activating means;
wherein when the valve is activated and in a first position, the second tube is closed and the gas/particle stream flows through the first tube to the surface; and when the valve is not activated and in a second position, the first tube is closed and the gas/particle stream flows through the second tube and is vented.

31. The apparatus of claim 30 which further comprises a waste container associated with the second flexible transmission tube.

* * * * *